US012324835B1

United States Patent
Yang et al.

(12) United States Patent
(10) Patent No.: US 12,324,835 B1
(45) Date of Patent: Jun. 10, 2025

(54) mRNA VACCINE ENCODING FUSION ANTIGEN AGAINST MPOX AND SEVERE ACUTE RESPIRATORY SYNDROME CORONAVIRUS 2

(71) Applicant: ACADEMY OF MILITARY MEDICAL SCIENCES, AMS, PLA, Beijing (CN)

(72) Inventors: Yilong Yang, Beijing (CN); Wei Chen, Beijing (CN); Junjie Xu, Beijing (CN); Xiaofan Zhao, Beijing (CN); Jun Zhang, Beijing (CN); Lihua Hou, Beijing (CN); Xiaodong Zai, Beijing (CN); Yu Li, Beijing (CN)

(73) Assignee: ACADEMY OF MILITARY MEDICAL SCIENCES, AMS, PLA, Beijing (CN)

( * ) Notice: Subject to any disclaimer, the term of this patent is extended or adjusted under 35 U.S.C. 154(b) by 0 days.

(21) Appl. No.: 19/026,296

(22) Filed: Jan. 16, 2025

(30) Foreign Application Priority Data

Mar. 5, 2024 (CN) .......................... 202410246021.5

(51) Int. Cl.
| | | |
|---|---|---|
| *A61K 9/50* | (2006.01) | |
| *A61K 39/215* | (2006.01) | |
| *A61K 39/275* | (2006.01) | |
| *A61K 47/69* | (2017.01) | |
| *C07K 14/005* | (2006.01) | |

(52) U.S. Cl.
CPC .......... *A61K 39/275* (2013.01); *A61K 9/5015* (2013.01); *A61K 39/215* (2013.01); *C07K 14/005* (2013.01)

(58) Field of Classification Search
None
See application file for complete search history.

(56) References Cited

FOREIGN PATENT DOCUMENTS

| | | |
|---|---|---|
| CN | 115725612 A | 3/2023 |
| CN | 116036259 A | 5/2023 |
| IN | 202111046243 A | 10/2023 |
| WO | 2022035621 A1 | 2/2022 |
| WO | 2023008553 A1 | 2/2023 |
| WO | 2023062515 A1 | 4/2023 |
| WO | 2023196935 A1 | 10/2023 |

OTHER PUBLICATIONS

Law et al (Vaccine, 2021, 39: 5769-5799) (Year: 2021).*
First Office Action in Chinese Application No. 202410246021.5 mailed on Apr. 8, 2024, 18 pages.
Decision to Grant a Patent in Chinese Application No. 202410246021.5 mailed on May 8, 2024, 10 pages.
Zhao, Xiaomeng et al., Research Advances on COVID-19 RNA Vaccine, Chinese Journal of Virology, 40(1): 151-159, 2024.
Wang, Mingwei et al., Research Progress on mRNA Technology and Its Application in Animal Disease, Chinese Journal of Veterinary Drug, 57(11): 62-71, 2023.
Li, Y. et al., Chain E, Spike protein S2', Genbank, 2023, 2 pages.
Swann H et al., Unverified: Synthetic construct clone h5(SARS-CoV2) sequence, EMBL, 2022, 5 pages.
Hills, R.A. et al., SpyTag-Kraken Quarter [synthetic construct], GenBank, 2024, 2 pages.
Hou, Fujun et al., mRNA vaccines encoding fusion proteins of monkeypox virus antigens protect mice from vaccinia virus challenge, nature communications, 14(1): 1-10, 2023.
Jiang, Fan et al., Developing a multiepitope vaccine for the prevention of SARS-CoV-2 and monkeypox virus co-infection: A reverse vaccinology analysis, International Immunopharmacology, 115: 1-18, 2023.

* cited by examiner

*Primary Examiner* — Misook Yu
*Assistant Examiner* — Marianne Dibrino
(74) *Attorney, Agent, or Firm* — PORUS IP LLC

(57) ABSTRACT

An mRNA molecule is disclosed. The mRNA molecule contains a polynucleotide encoding an M1R antigen of Mpox and a polynucleotide encoding an RBD antigen of severe acute respiratory syndrome coronavirus 2 (SARS-CoV-2), and further contains a polynucleotide encoding an A35R antigen of Mpox. An application of the mRNA molecule in the preparation of an mRNA vaccine against Mpox or SARS-CoV-2 is further disclosed. Compared to an mRNA vaccine encoding separately corresponding antigens, the provided mRNA vaccine encoding a fusion antigen can induce considerable or even higher-level neutralizing antibody responses against Mpox and SARS-CoV-2, and provides 100% immune protection against the lethal challenge of ectromelia virus. The vaccine is obtained by synthesizing a single mRNA molecule and encapsulating the single mRNA within lipid nanoparticles. Therefore, the single-component fusion mRNA vaccine has a wider application prospect than multivalent mRNA vaccine compositions.

18 Claims, 10 Drawing Sheets
Specification includes a Sequence Listing.

FIG. 10 ns# mRNA VACCINE ENCODING FUSION ANTIGEN AGAINST MPOX AND SEVERE ACUTE RESPIRATORY SYNDROME CORONAVIRUS 2

CROSS REFERENCE TO THE RELATED APPLICATIONS

This application is based upon and claims priority to Chinese Patent Application No. 202410246021.5, filed on Mar. 5, 2024, the entire contents of which are incorporated herein by reference.

SEQUENCE LISTING

The instant application contains a Sequence Listing which has been submitted electronically in XML format and is hereby incorporated by reference in its entirety. The XML copy, created on Mar. 17, 2025, is named "2025-03-17-Sequence listing-69705-H005US00.xml," and is 26,604 bytes in size.

TECHNICAL FIELD

The present disclosure relates to the technical field of biology engineering, and in particular, to an mRNA vaccine against Mpox and severe acute respiratory syndrome coronavirus 2 (SARS-CoV-2).

BACKGROUND

In the context of the long-term pandemic of COVID-19, the emergence of other emerging infectious diseases continuously poses new threats to humans. Orthopoxvirus includes smallpox virus, Mpox, vaccinia virus, ectromelia virus, etc., with a very close evolutionary distance. Although the current Mpox is mainly confined to certain specific populations, immune dysfunction caused by SARS-CoV-2 infection may lead to the expansion of the susceptible population of Mpox. At present, there have been cases of co-infection of SARS-CoV-2 and Mpox. Therefore, it is necessary to develop a single-component fusion vaccine against Mpox and SARS-CoV-2. The vaccine can enhance the immune protection against SARS-CoV-2 by boosting immunization while generating immune responses to the orthopoxvirus.

S protein is the most important protective antigen of SARS-CoV-2, as well as a core component of the recombinant vaccine against SARS-CoV-2. By contrast, Mpox has a more complex antigen spectrum. At present, most recombinant monkeypox vaccines adopt a multivalent strategy. Aiming at different antigens such as M1R, A35R, H3L, A29L, B6R, E8L, etc., a combinatorial design is carried out to form a multi-component vaccine. The mRNA vaccine has the technical advantages of rapid synthesis and high immunogenicity. An objective of the present disclosure is to provide an mRNA vaccine encoding a single-component fusion antigen based on mRNA technology, which can induce high-level antibody responses against antigens of Mpox and SARS-CoV-2 simultaneously.

SUMMARY

In view of this, the present disclosure first provides an mRNA molecule. The mRNA molecule contains an mRNA encoding an M1R antigen of Mpox and an mRNA encoding an RBD antigen of severe acute respiratory syndrome coronavirus 2 (SARS-CoV-2).

In a preferred embodiment, a sequence of a polypeptide encoded by the mRNA molecule is shown in SEQ ID NO: 2.

In a more preferred embodiment, a sequence of a polynucleotide encoded by the mRNA molecule is shown in SEQ ID NO: 1.

In another preferred embodiment of the present disclosure, the mRNA molecule further contains an mRNA encoding an A35R antigen of Mpox.

In a more preferred embodiment, a sequence of a polypeptide encoded by the mRNA molecules is shown in SEQ ID NO: 4.

More preferably, a sequence of a polynucleotide encoded by the mRNA molecule is shown in SEQ ID NO: 3.

In a more preferred embodiment of the present disclosure, a 5' end of the mRNA molecule further contains a promoter and a 5'untranslated region (UTR), and a 3' end of the mRNA further contains a 3'UTR, a stop codon, poly (A), and BspQI restriction enzyme sites in series.

Especially preferably, a sequence of the promoter is shown in SEQ ID NO: 5, a sequence of the 5'UTR is shown in SEQ ID NO: 6, a sequence of the 3'UTR is shown in SEQ ID NO: 7, a sequence of the stop codon is TGATAATAG, a sequence of the BspQI restriction enzyme sites in series is GAAGAGC, and a length of poly (A) is 110 nucleotides.

In a preferred embodiment, a sequence of the mRNA molecule is shown in SEQ ID NO: 14 or SEQ ID NO: 15.

In a more preferred embodiment, the 5' end of the mRNA molecule further contains a Cap1 cap structure.

Secondly, the present disclosure provides a lipid nanoparticle encapsulating the mRNA molecule.

Thirdly, the present disclosure provides a preparation method for the lipid nanoparticle, including the following steps:
(a) forming a lipid mixture with heptadecan-9-yl 8-((2-hydroxyethyl)(6-oxo-6-(undecyloxy)hexyl)amino)octanoate, 1, 2-distearoyl-sn-glycero-3-phosphocholine, methoxy polyethylene glycol-dimyristoyl glycerol, and cholesterol according to a molar ratio of 50:10:1.5: 38.5, and preparing a mRNA solution containing the mRNA molecule; and
(b) mixing the lipid mixture with the mRNA solution obtained in step (a).

In a more preferred embodiment, in step (b), a mass ratio of the lipid mixture to the mRNA solution is 1:3.

Lastly, the present disclosure provides an application of the mRNA in preparing an mRNA vaccine against Mpox or SARS-CoV-2.

Compared to an mRNA vaccine encoding separately corresponding antigens, the mRNA vaccine encoding a fusion antigen provided by the present disclosure can induce considerable or even higher-level neutralizing antibody responses against Mpox and SARS-CoV-2, and provides 100% immune protection against the lethal challenge of the ectromelia virus. In addition, the preparation of the single-component fusion mRNA vaccine is simple, and the single-component fusion mRNA vaccine is obtained by only synthesizing a single mRNA molecule and encapsulating the single mRNA molecule within lipid nanoparticles. Therefore, the single-component fusion mRNA vaccine has a wider application prospect than multivalent mRNA vaccine compositions.

BRIEF DESCRIPTION OF THE DRAWINGS

FIG. 10 is a chart illustrating levels of the immune protection of mRNA candidate vaccines against the lethal challenge of the ectromelia virus.

DETAILED DESCRIPTION OF THE EMBODIMENTS

Figure 1:
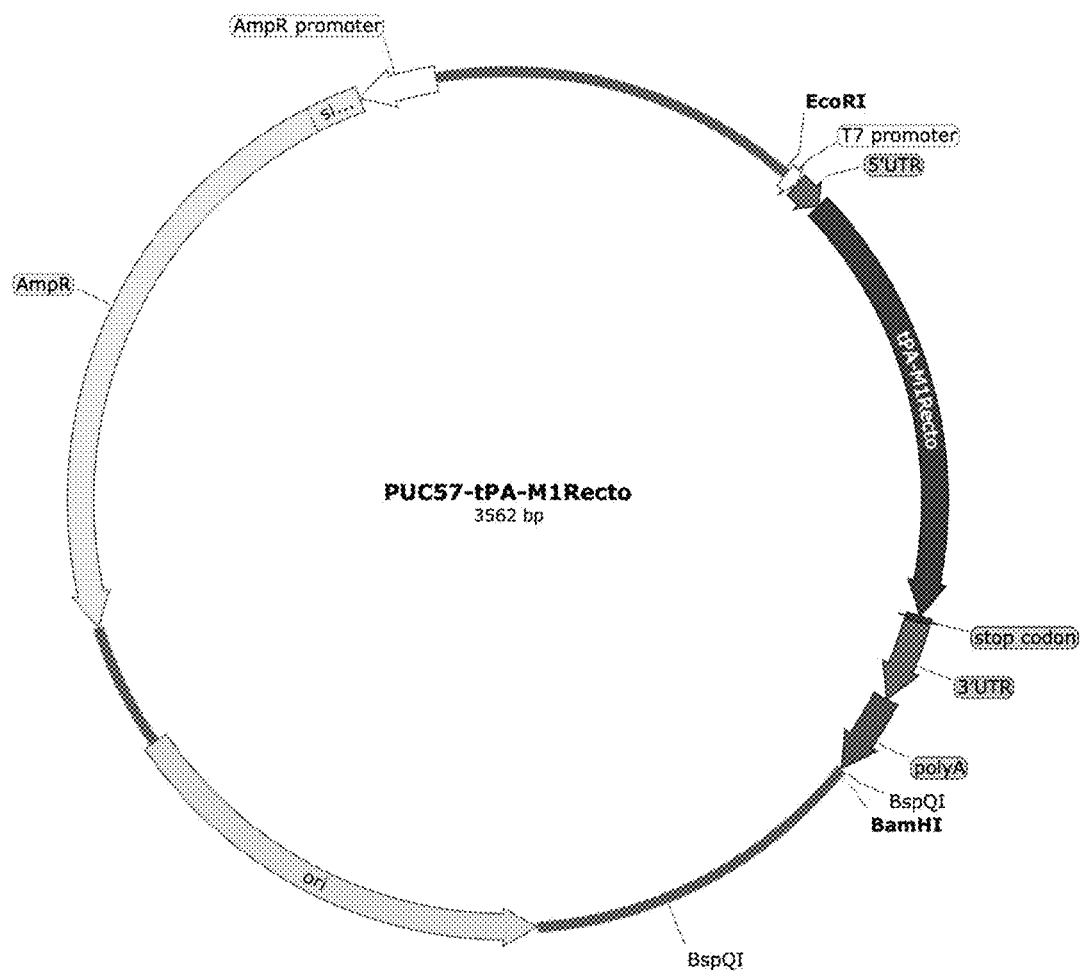
FIG. 1 is a schematic diagram of a template plasmid PUC57-tPA-M1R$_{ecto}$ for mRNA synthesis.
Figure 2:
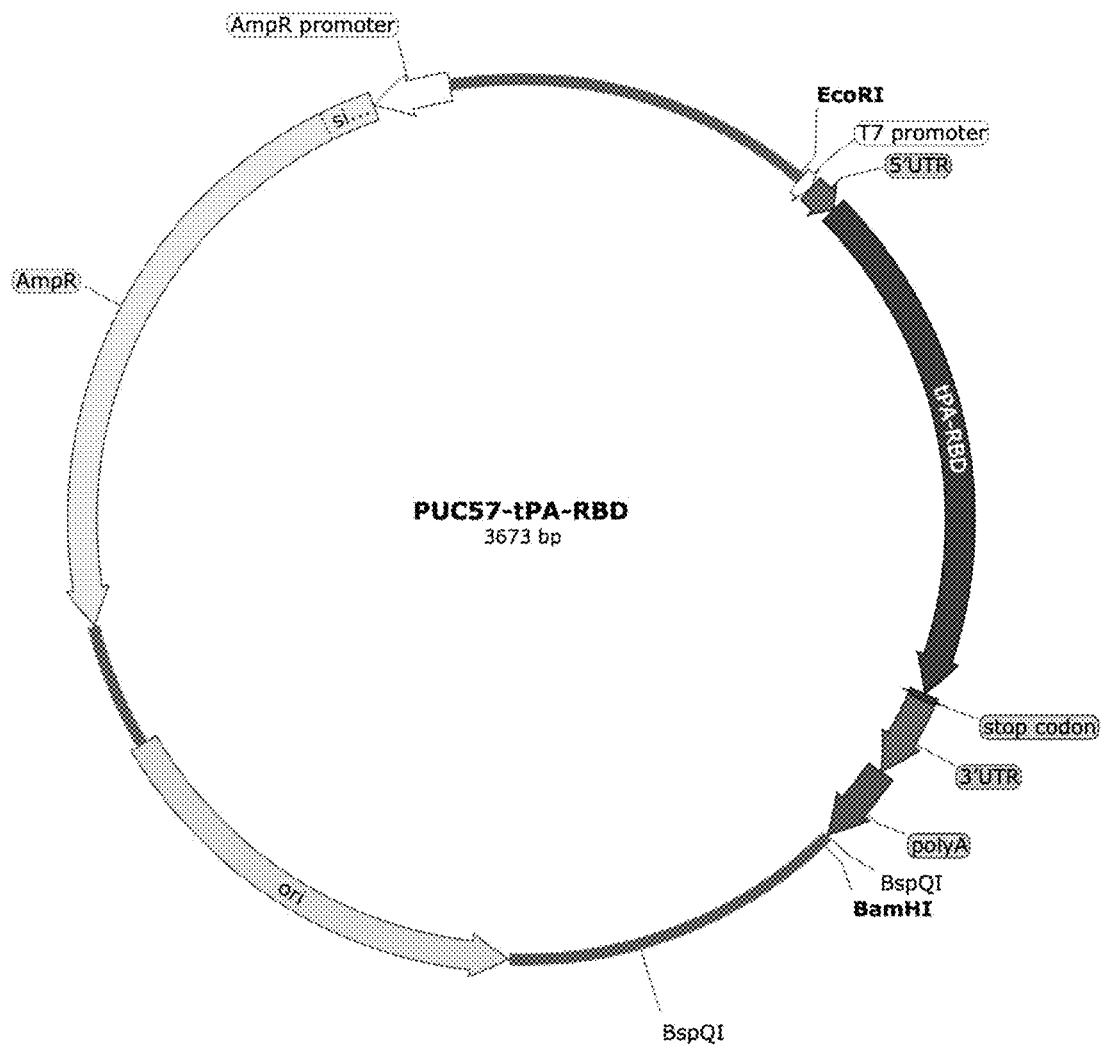
FIG. 2 is a schematic diagram of a template plasmid PUC57-tPA-RBD for mRNA synthesis.
Figure 3:
FIG. 3 is a schematic diagram of a template plasmid PUC57-tPA-A35R$_{ecto}$ for mRNA synthesis.
Figure 4:
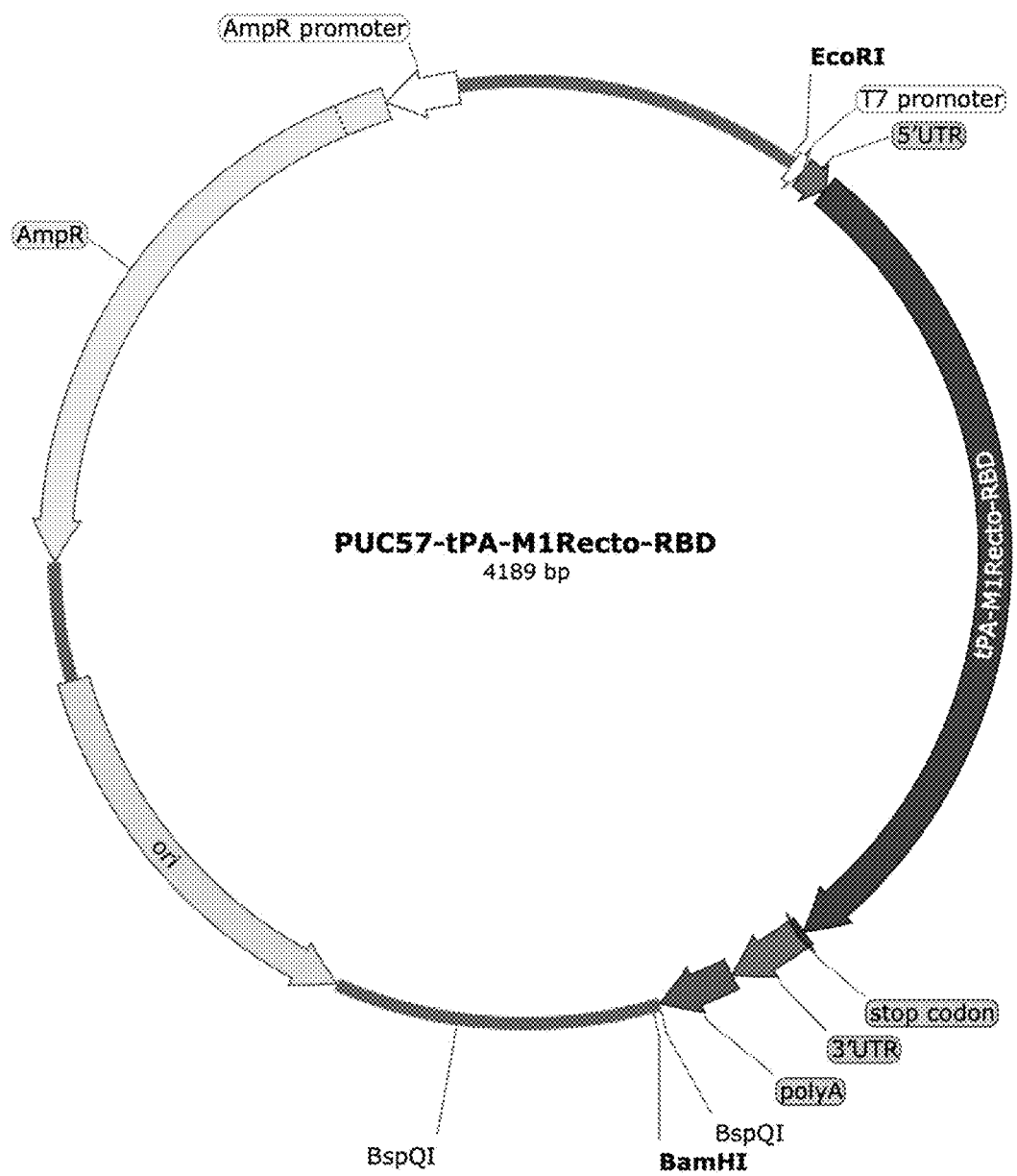
FIG. 4 is a schematic diagram of a template plasmid PUC57-tPA-M1R$_{ecto}$-RBD for mRNA synthesis.
Figure 5:
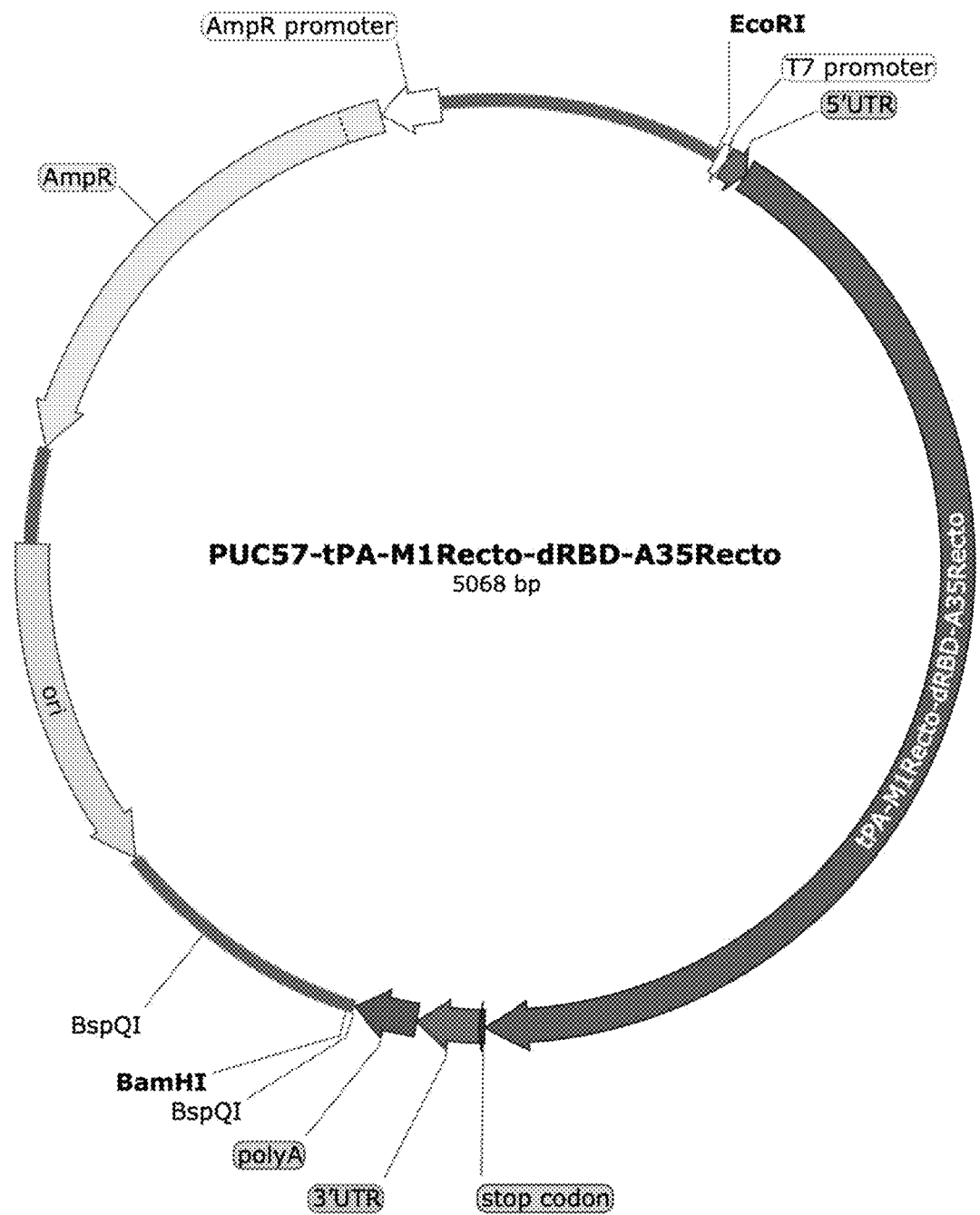
FIG. 5 is a schematic diagram of a template plasmid PUC57-tPA-M1R$_{ecto}$-dRBD-A35R$_{ecto}$ for mRNA synthesis.

In the following, the advantages and characteristics of the present disclosure will be more clearly described in combination with the embodiments to further describe the present disclosure. However, these embodiments are merely exemplificative, which do not constitute any restriction on the scope of protection limited by the claims of the present disclosure.

Embodiment 1 Preparation of mRNA Vaccines (1) Constructing Template Plasmids The tPA signal peptide was fused to the N-terminus of encoded antigens M1R$_{ecto}$, RBD, A35R$_{ecto}$, M1R$_{ecto}$-RBD, and M1R$_{ecto}$-dRBD-A35R$_{ecto}$, respectively, through sequence optimization, the obtained target nucleotide sequences were SEQ ID NO: 8, SEQ ID NO: 9, SEQ ID NO: 10, SEQ ID NO: 1, and SEQ ID NO: 3, respectively. According to the 5'→3' direction, a T7 promoter (SEQ ID NO: 5), a 5'UTR (SEQ ID NO: 6), target nucleotides, a 3'UTR (SEQ ID NO: 7), a stop codon (TGATAATAG), a poly (A) sequence of 110 nucleotides (nt), BspQI restriction enzyme sites (GAAGAGC) were connected and cloned into PUC57 plasmids, to obtain the template plasmids (FIGS. 1-5).

(2) Linearization of the Template Plasmids

In a 200 µL reaction system containing 20 µg template plasmids, 10 µL BspQI enzyme (10 U/µL), and 20 µL 10×BspQ IBuffer and Nuclease-Free H$_2$O, a reaction was performed at 50° C. for 1 h. The linearized template plasmids were purified with the phenol-chloroform extraction method, an equal volume of phenol-chloroform (Tris saturated phenol:chloroform:isopentanol=25:24:1) was added to the DNA solution, and fully and evenly mixed; at room temperature, a centrifugal acceleration was adjusted to 12000 g for performing centrifuge for 10 min; the upper aqueous phase was extracted carefully, and an equal volume of chloroform solution (chloroform:isopentanol=24:1) was added, and fully and evenly mixed; and after centrifugation (ditto), the supernatant was extracted carefully and detected for DNA concentration.

(3) In Vitro Transcription of mRNA and Purification

In vitro transcription was performed on mRNA molecules encoding M1R$_{ecto}$, RBD, A35R$_{ecto}$, M1R$_{ecto}$-RBD, and M1R$_{ecto}$-dRBD-A35R$_{ecto}$, a modification ratio of N1-methylpseudourine to uracil was 100%. In a 100 µL reaction system containing 5 µg linearized plasmids, 10 µL T7 RNA Polymerase (50 U/µL), 5 µL inorganic pyrophosphatase (0.1 U/µL), L RNase Inhibitor (40 U/µL), 10 µL 10×Reaction buffer, 10 µL ATP (100 mM), 10 µL GTP (100 mM), 10 µL m1ψ/UTP (100 mM), and 10 µL CTP (100 mM) and Nuclease-Free H$_2$O (the above reagents were purchased from Nanjing Vazyme Biotech Co., Ltd.), after being fully and evenly mixed, a reaction was performed at 37° C. for 2 h. Subsequently, 5 µL DNase I (1 U/µL) was added to the reaction system for reacting at 37° C. for 15 min, to remove the DNA templates for transcription. The transcription products of mRNA were purified with the phenol-chloroform extraction method as described above.

(4) mRNA Capping and Purification

Figure 6:
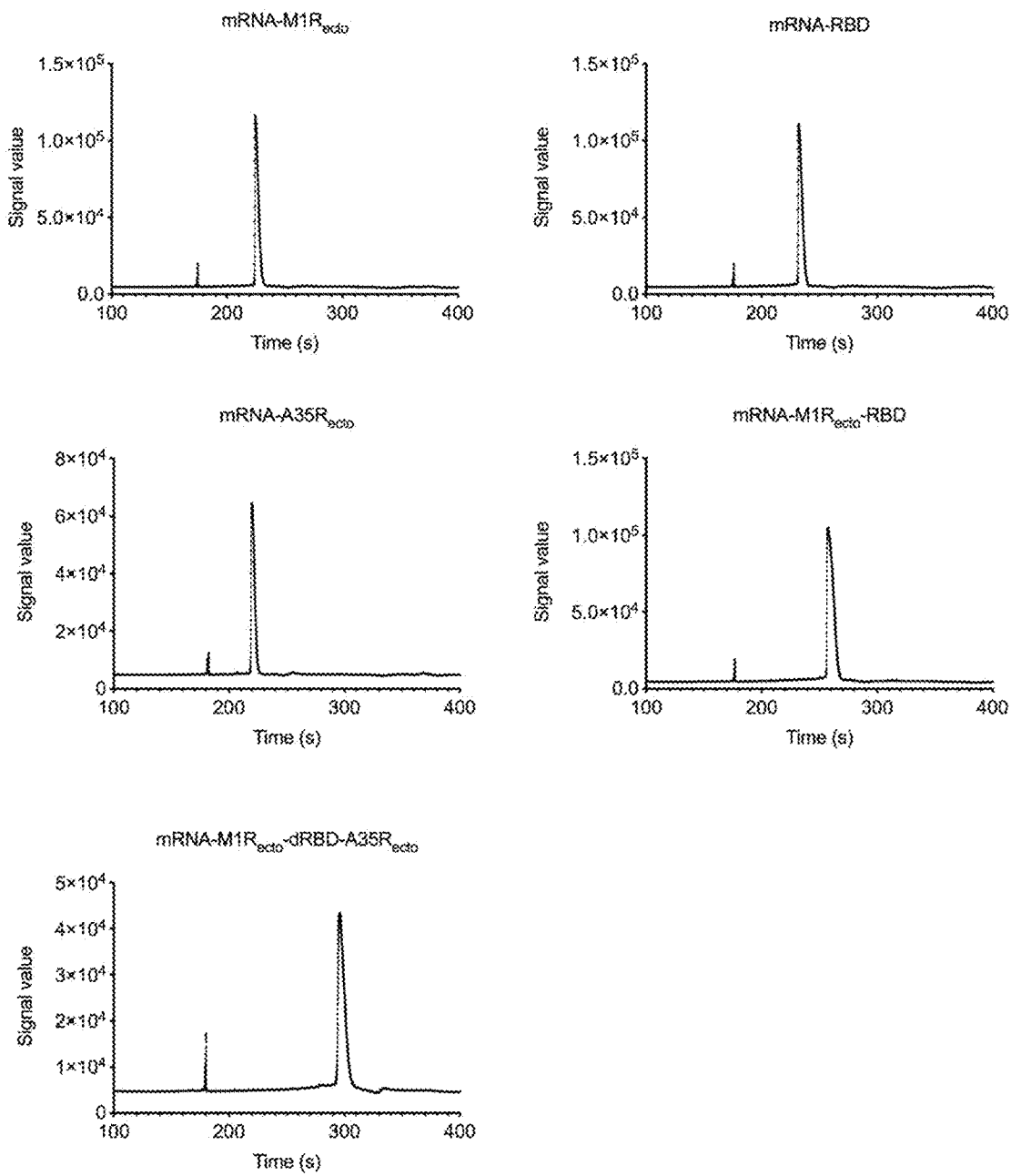
FIG. 6 is an electrophoretic pattern illustrating synthesized mRNA molecules characterized by capillary electrophoresis.

In a 100 µL reaction system containing 200 µg transcribed mRNA, 50 µL 10×Capping Reaction buffer, 25 µL GTP (10 mM), 25 µL SAM (4 mM), 25 µL Vaccinia Capping Enzyme (10 U/µL), and 25 µL 2'-O-Methyltransferase (50 U/µL) and Nuclease-Free H$_2$O (the above reagents were purchased from Nanjing Vazyme Biotech Co., Ltd.), after being fully and evenly mixed, a reaction was performed at 37° C. for 1 h, and the transcription products of mRNA were purified with phenol-chloroform extraction method as described above. The molecular integrity of the transcription products of mRNA was detected by capillary electrophoresis (FIG. 6), and the results shows that the size of the prepared products including mRNA-M1R$_{ecto}$ (SEQ ID NO:11), mRNA-RBD (SEQ ID NO:12), RNA-A35R$_{ecto}$ (SEQ ID NO:13), mRNA-M1R$_{ecto}$-RBD (SEQ ID NO:14), and mRNA-M1R$_{ecto}$-dRBD-A35R$_{ecto}$ (SEQ ID NO:15) is in line with expectations, with a purity of more than 90%.

(5) the Encapsulation of mRNA within Lipid Nanoparticles

Figure 7:
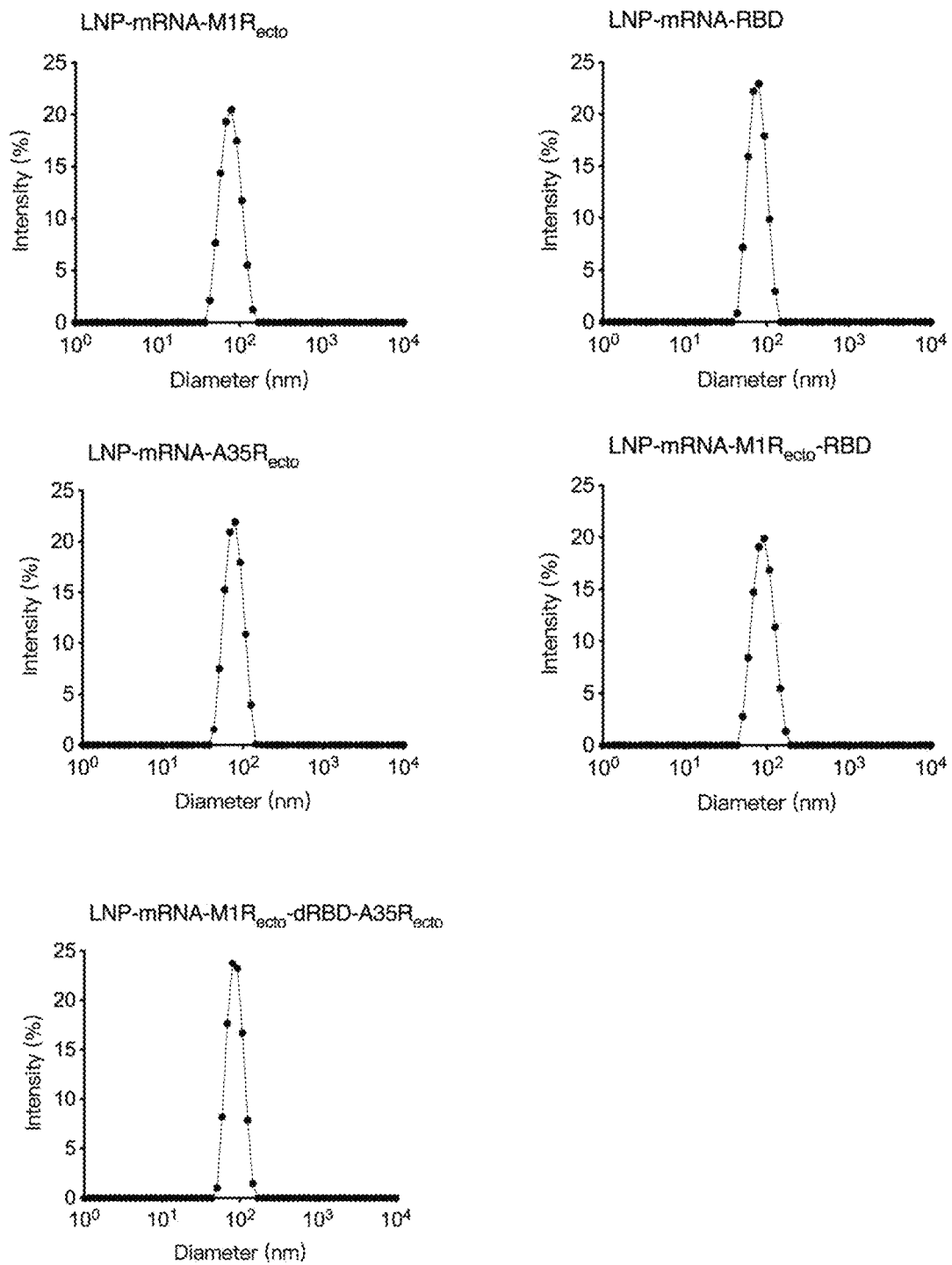
FIG. 7 is a particle size distribution chart illustrating lipid nanoparticles encapsulated-mRNA vaccines characterized by dynamic light scattering.

SM-102 (heptadecan-9-yl 8-((2-hydroxyethyl)(6-oxo-6-(undecyloxy)hexyl)amino)octanoate, purchased from Xiamen Sinopeg Biotech Co., Ltd.), DSPC (1, 2-distearoyl-sn-glycero-3-phosphocholine, purchased from Xiamen Sinopeg Biotech Co., Ltd.), DMG-PEG2000 (methoxy polyethylene glycol-dimyristoyl glycerol, purchased from Xiamen Sinopeg Biotech Co., Ltd.), and cholesterol (purchased from AVT (Shanghai) Pharmaceutical Tech Co., Ltd.) were dissolved in ethanol at a molar ratio of 50:10:1.5:38.5, to prepare ethanol phase; and the mRNA molecules were dissolved in 50 mM sodium acetate buffer (pH=5.0), to prepare aqueous phase; when performing the encapsulation by microfluidics, the volume ratio of the ethanol phase to the aqueous phase was 1:3, and the total flow rate was 12 mL/min. After the encapsulation, ultrafiltration concentration and buffer exchange with PBS buffer were performed, after the encapsulation rate and effective concentration were detected, the obtained products were stored at 4° C. Dynamic light scattering (DLS) measurements show that the mRNA vaccines encapsulated within lipid nanoparticles have a uniform particle size distribution (FIG. 7), the average size of LNP-mRNA-M1R$_{ecto}$, LNP-mRNA-RBD, LNP-mRNA-A35R$_{ecto}$, LNP-mRNA-M1R$_{ecto}$-RBD, and LNP-mRNA-M1R$_{ecto}$-dRBD-A35R$_{ecto}$ were 74.40 nm, 73.82 nm, 73.27 nm, 85.91 nm, and 83.93 nm, respectively, and the dispersion coefficients were all less than 0.05.

Embodiment 2 Immune Response of the mRNA Vaccines

In a BALB/c mouse model, 5 µg of five candidate vaccines including mRNA-M1R$_{ecto}$, mRNA-RBD, mRNA- A35R$_{ecto}$, mRNA-M1R$_{ecto}$-RBD, mRNA-M1R$_{ecto}$-dRBD-A35R$_{ecto}$ were inoculated on day 0 and day 14 by intramuscular injection, respectively (with 6 mice in each group), blood samples were collected for serum collection on the 14 th and 28 th day, the specific IgG antibody and neutralizing antibody levels were detected, and the lethal challenge of the ectromelia virus was carried out on day 28.

(1) Specific IgG Antibody Response

The recombinant proteins of M1R (Sino Biological, Inc. (China), 40904-V07H), A35R (Sino Biological, Inc. (China), 40886-V07E), and RBD (Sino Biological, Inc. (China), 40592-V08H136) were diluted to the concentration of 1 μg/mL, which was coated in 96-well plates overnight, after blocking, the IgG antibody titer was detected by enzyme-linked immunosorbent assay, and statistically analyzed by two-way ANOVA with Šidák's multiple comparison test.

In the specific antibody response against M1R, 14 days after a single immunization with mRNA-M1R$_{ecto}$-RBD and mRNA-M1R$_{ecto}$-dRBD-A35R$_{ecto}$, the geometry mean values of IgG antibody titer were 19454 and 7798, respectively, and the antibody titer was significantly increased 14 days after boosting immunization (28 days after the first immunization), the geometric mean values were 3647529 and 486407, respectively, which were 20 times (P<0.0001) and 3 times higher than mRNA-M1R$_{ecto}$ antibody titer (162181).

In the specific antibody response against RBD, 14 days after a single immunization with mRNA-M1R$_{ecto}$-RBD and mRNA-M1R$_{ecto}$-dRBD-A35R$_{ecto}$, both geometry mean values of IgG antibody titer were 16218, and the antibody titer was significantly increased 14 days after boosting immunization (28 days after the first immunization), the geometric mean values were 2023019 and 1093956, respectively, which were 14 times (P<0.0001) and 7 times (P=0.0002) higher than the mRNA-RBD antibody titer (145881).

Figure 8:
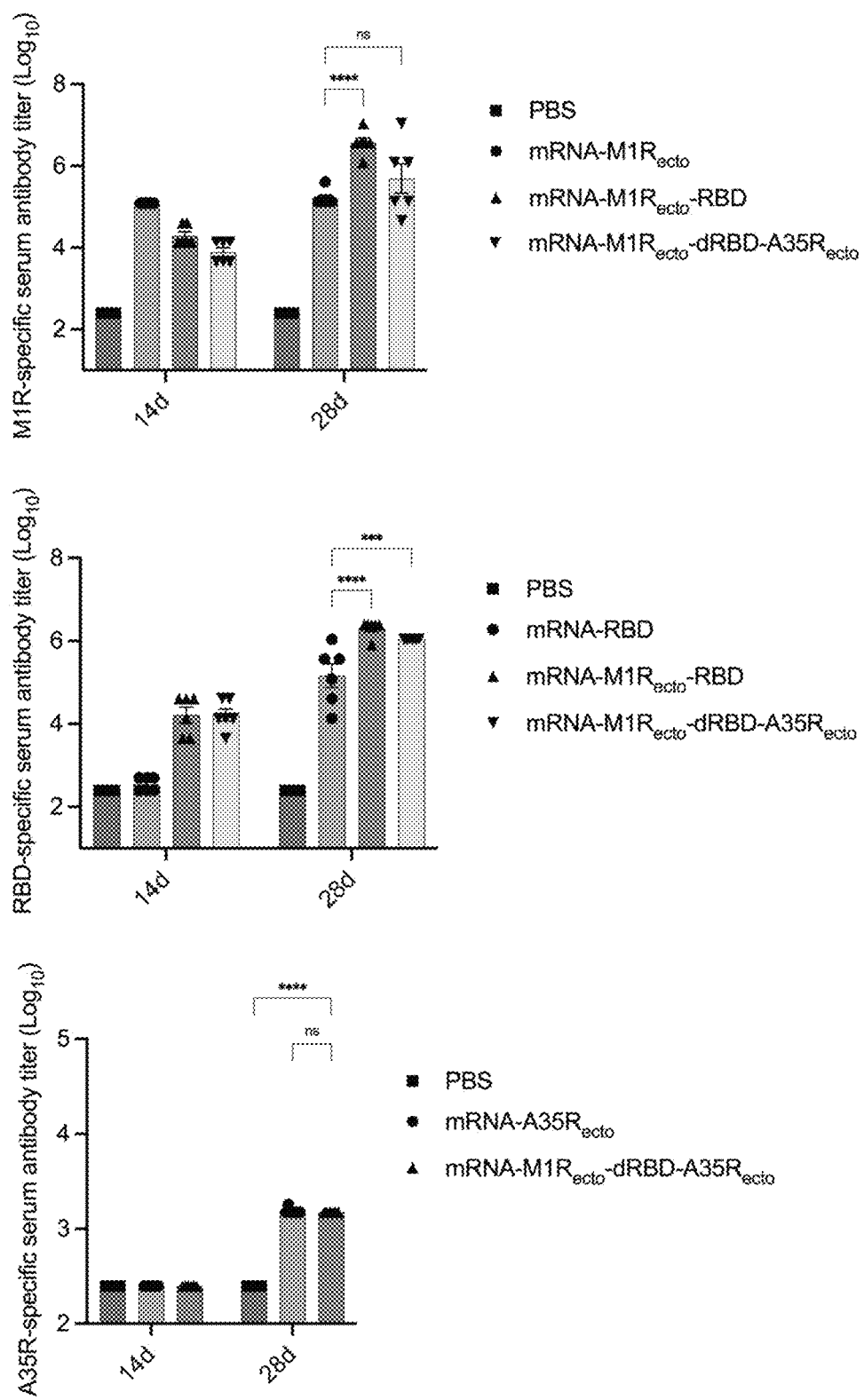
FIG. 8 is a chart illustrating levels of specific antibodies induced by mRNA candidate vaccines.
Figure 9:
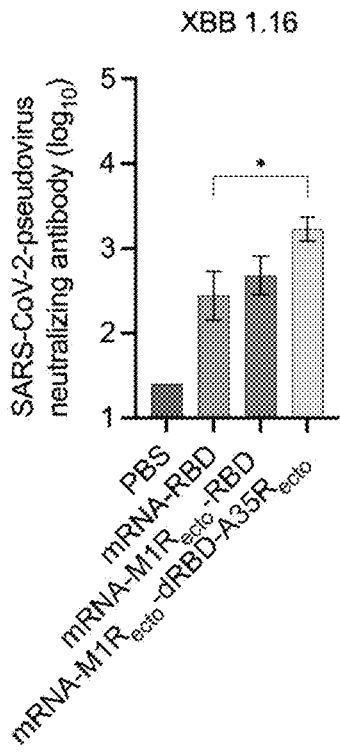
FIG. 9 is a chart illustrating neutralizing antibody levels against SARS-CoV-2 pseudovirus induced by mRNA candidate vaccines.
Figure 9:
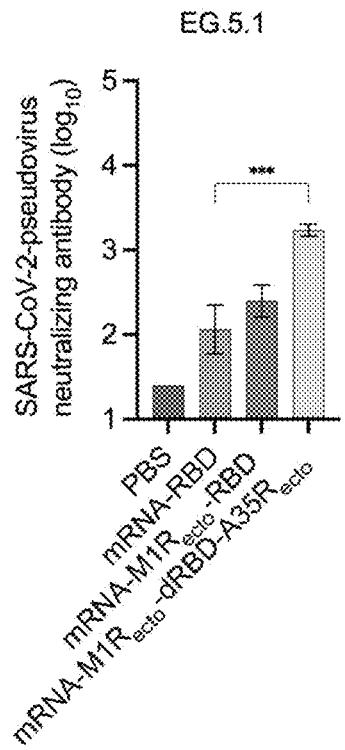

In the specific antibody response against A35R, the geometric mean value of IgG antibody titer 28 days after boosting immunization with mRNA-M1R$_{ecto}$-dRBD-A35R$_{ecto}$ was 1500, which was not statistically different from the mRNA-A35R$_{ecto}$, but significantly higher than the PBS control group (P<0.001). (FIG. 8).

(2) SARS-CoV-2-Pseudovirus Neutralizing Antibody Response

Through infection of 293 cells stably express human ACE2 with SARS-CoV-2-pseudovirus, neutralizing antibody levels in serum against SARS-CoV-2-pseudovirus were detected 14 days after boosting immunization (28 days after the first immunization). For the pseudovirus of SARS-CoV-2 Omicron variants XBB.1.16, the geometry mean values of neutralizing antibody titers against SARS-CoV-2-pseudovirus with mRNA-M1R$_{ecto}$-RBD and mRNA-M1R$_{ecto}$-dRBD-A35R$_{ecto}$ reached 480 and 1694, which were 2 times and 6 times (p=0.027) higher than the neutralizing antibody titer with mRNA-RBD (277), respectively. For the pseudovirus of SARS-CoV-2 Omicron variants EG.5.1, the geometry mean values of neutralizing antibody titers against SARS-CoV-2-pseudovirus with mRNA-M1R$_{ecto}$-RBD and mRNA-M1R$_{ecto}$-dRBD-A35R$_{ecto}$ reached 251 and 1714, which were 2 times (no statistical difference) and 15 times (p=0.0004) of the neutralizing antibody titer with mRNA-RBD (115), respectively. The above results indicate that the neutralizing antibody level against SARS-CoV-2, which was produced by activation of mRNA-M1R$_{ecto}$-RBD, is equivalent to that produced by activation of mRNA-RBD, while compared with mRNA-RBD, RNA-M1R$_{ecto}$-dRBD-A35R$_{ecto}$ can induce a higher neutralizing antibody level against SARS-CoV-2.

(3) Protection Against the Lethal Challenge of Ectromelia Virus

Figure 10:
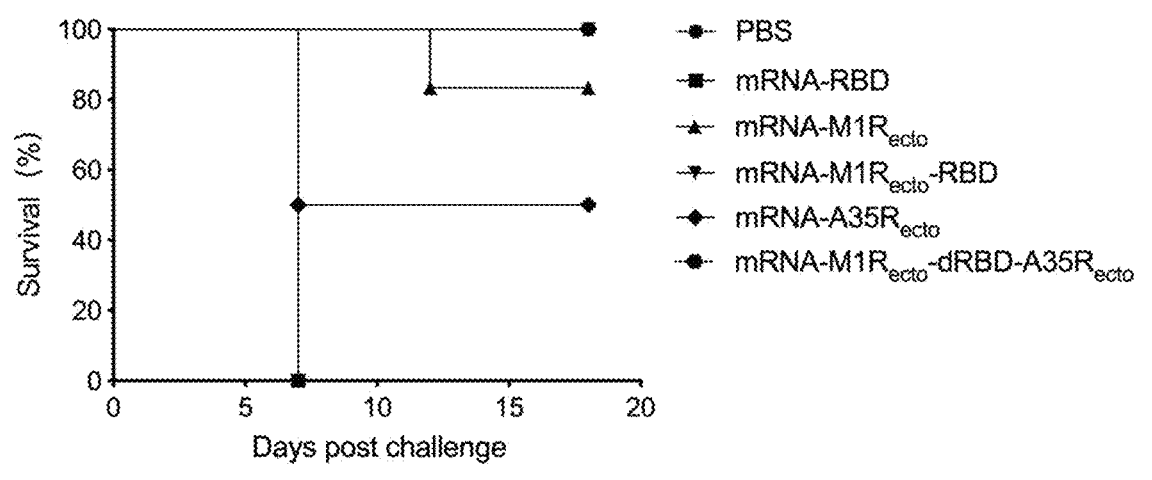

Through infection of BS-C-1 cells with ectromelia virus, the ectromelia virus (ATCC VR-1374) was amplified and cultured. 28 days after the first immunization, each mouse was challenged intraperitoneally with 200 PFU ectromelia virus, the survival of mice was monitored within 18 days, and statistically analyzed by Log-rank (Mantel-Cox) test. In a lethal challenge experiment, the survival rates of mRNA-M1R$_{ecto}$-RBD and mRNA-M1R$_{ecto}$-dRBD-A35R$_{ecto}$ immunized groups were both 100%, compared with the PBS control group (with a survival rate of 0%), which had significant immune protection (p=0.0009). The above results confirm that the mRNA vaccines encoding M1R$_{ecto}$-RBD and M1R$_{ecto}$-dRBD-A35R$_{ecto}$ can provide complete immune protection against the lethal challenge of orthopoxvirus. (FIG. 10).

What is claimed is:

1. An mRNA molecule, wherein the sequence of a polypeptide encoded by the mRNA molecule is shown in SEQ ID NO: 2.

2. The mRNA molecule according to claim 1, wherein the sequence of the mRNA molecule is shown in SEQ ID NO: 1.

3. An mRNA molecule, wherein the sequence of a polypeptide encoded by the mRNA molecule is shown in SEQ ID NO: 4.

4. The mRNA molecule according to claim 3, wherein the sequence of the mRNA molecule is shown in SEQ ID NO: 3.

5. The mRNA molecule according to claim 1, wherein the 5' end of the mRNA molecule contains a promoter and a 5' untranslated region (UTR), and the 3' end of the mRNA contains a 3'UTR, a stop codon, poly (A), and BspQI restriction enzyme sites in series.

6. The mRNA molecule according to claim 5, wherein the sequence of the promoter is shown in SEQ ID NO: 5, a sequence of the 5'UTR is shown in SEQ ID NO: 6, the sequence of the 3'UTR is shown in SEQ ID NO: 7, the sequence of the stop codon is TGATAATAG, the sequence of the BspQI restriction enzyme sites in series is GAAGAGC, and the length of poly (A) is 110 nucleotides.

7. The mRNA molecule according to claim 6, wherein the sequence of the mRNA molecule is shown in SEQ ID NO: 14 or SEQ ID NO: 15.

8. The mRNA molecule according to claim 7, wherein the 5' end of the mRNA molecule is connected to a Cap1 cap structure.

9. A lipid nanoparticle encapsulating the mRNA molecule according to claim 8.

10. A preparation method of the lipid nanoparticle according to claim 9 comprising the following steps:
(a) forming a lipid mixture with heptadecan-9-yl 8-((2-hydroxyethyl)(6-oxo-6-(undecyloxy)hexyl)amino)octanoate, 1, 2-distearoyl-sn-glycero-3-phosphocholine, methoxy polyethylene glycol-dimyristoyl glycerol, and cholesterol according to a molar ratio of 50:10:1.5:38.5, and preparing a mRNA solution containing the mRNA molecule according to claim 6; and
(b) mixing the lipid mixture with the mRNA solution obtained in step (a).

11. The preparation method according to claim 10, wherein in step (b), a mass ratio of the lipid mixture to the mRNA solution is 1:3.

12. The mRNA molecule according to claim 3, wherein the 5' end of the mRNA molecule contains a promoter and a 5' untranslated region (UTR), and the 3' end of the mRNA contains a 3'UTR, a stop codon, poly (A), and BspQI restriction enzyme sites in series.

13. The mRNA molecule according to claim 12, wherein the sequence of the promoter is shown in SEQ ID NO: 5, the sequence of the 5'UTR is shown in SEQ ID NO: 6, the sequence of the 3'UTR is shown in SEQ ID NO: 7, the sequence of the stop codon is TGATAATAG, the sequence of the BspQI restriction enzyme sites in series is GAAGAGC, and the length of poly (A) is 110 nucleotides.

14. The mRNA molecule according to claim 13, wherein the sequence of the mRNA molecule is shown in SEQ ID NO: 14 or SEQ ID NO: 15.

15. The mRNA molecule according to claim 14, wherein the 5' end of the mRNA molecule is connected to a Cap1 cap structure.

16. A lipid nanoparticle encapsulating the mRNA molecule according to claim 15.

17. A preparation method of the lipid nanoparticle according to claim 16 comprising the following steps:
(a) forming a lipid mixture with heptadecan-9-yl 8-((2-hydroxyethyl)(6-oxo-6-(undecyloxy)hexyl)amino)octanoate, 1, 2-distearoyl-sn-glycero-3-phosphocholine, methoxy polyethylene glycol-dimyristoyl glycerol, and cholesterol according to a molar ratio of 50:10:1.5:38.5, and preparing a mRNA solution containing the mRNA molecule according to claim 13; and
(b) mixing the lipid mixture with the mRNA solution obtained in step (a).

18. The preparation method according to claim 17, wherein in step (b), a mass ratio of the lipid mixture to the mRNA solution is 1:3.

* * * * *

SEQUENCE LISTING

```
Sequence total quantity: 15
SEQ ID NO: 1           moltype = DNA  length = 1212
FEATURE                Location/Qualifiers
source                 1..1212
                       mol_type = other DNA
                       organism = unidentified
SEQUENCE: 1
atggacgcca tgaagagagg cctgtgctgt gtgctgctgc tgtgcggcgc cgtgttcgtg   60
tccaacagca tgggcgccgc cgccagcatc cagaccacag tgaataccct gagcgagagg  120
atcagctcca agctggagca ggaggccaat gccagcgccc agaccaagtg tgatatcgag  180
atcggcaatt tctacatcag gcagaaccac ggctgtaaca tcacagtgaa gaacatgtgc  240
tccgccgatg ccgatgccca gctggacgcc gtgctgtccg ccgctaccga gacctacagc  300
ggcctgacac ctgagcagaa ggcctacgtg cctgccatgt tcaccgccgc cctgaacatc  360
cagacctccg tgaataccgt ggtgagggat ttcgagaatt acgtgaagca gacatgcaac  420
agcagcgccg tggtggataa caagctgaag atccagaatg tgatcatcga cgagtgctac  480
ggcgcccccg gcagccctac aaacctggag tttatcaaca caggcagcag caagggcaac  540
tgtgccatca aggccctgat gcagctgaca accaaggcca caacaaaa cctgtgccca  600
tttcacgagg tgttcaacgc cacaaccttc gcctccgtgt acgcctggaa taggaagagg  660
atctccaact gcgtggccga ctactccgtg atctacaact tcgcccccct tttcgccttt  720
aagtgttacg gcgtgagccc tacaaagctg aatgacctgt gtttcaccaa tgtgtacgcc  780
gattcctttg tgatcagagg caacgaggtg tcccagatcg ccccggcca gacaggcaat  840
atcgccgact acaactacaa gctgcctgat gacttcaccg gctgtgtgat cgcctggaat  900
agcaacaagc tggattccaa ggtgggcggc aactacaact acctgtacag gctgttcaga  960
aagagcaagc tgaagccttt tgagagagac atctccaccg agatctacca ggccggcaac 1020
agaccctgta atggcgtgga gggcttcaat tgctactccc ccctgcagtc ctacggcttc 1080
```

```
aggcccacat acggcgtggg ccaccagccc tacagagtgg tggtgctgag ctttgagctg 1140
ctgcacgccc ctgccaccgt gtgcggacca agaagtcca caaatctggt gaagaacaag 1200
tgcgtgaact tt                                                     1212

SEQ ID NO: 2           moltype = AA   length = 404
FEATURE                Location/Qualifiers
source                 1..404
                       mol_type = protein
                       organism = unidentified
SEQUENCE: 2
MDAMKRGLCC VLLLCGAVFV SNSMGAAASI QTTVNTLSER ISSKLEQEAN ASAQTKCDIE  60
IGNFYIRQNH GCNITVKNMC SADADAQLDA VLSAATETYS GLTPEQKAYV PAMFTAALNI 120
QTSVNTVVRD FENYVKQTCN SSAVVDNKLK IQNVIIDECY GAPGSPTNLE FINTGSSKGN 180
CAIKALMQLT TKATTTNLCP FHEVFNATTF ASVYAWNRKR ISNCVADYSV IYNFAPFFAF 240
KCYGVSPTKL NDLCFTNVYA DSFVIRGNEV SQIAPGQTGN IADYNYKLPD DFTGCVIAWN 300
SNKLDSKVGG NYNYLYRLFR KSKLKPFERD ISTEIYQAGN RPCNGVEGFN CYSPLQSYGF 360
RPTYGVGHQP YRVVVLSFEL LHAPATVCGP KKSTNLVKNK CVNF                  404

SEQ ID NO: 3           moltype = DNA   length = 2091
FEATURE                Location/Qualifiers
source                 1..2091
                       mol_type = other DNA
                       organism = unidentified
SEQUENCE: 3
atggatgcca tgaagagagg cctgtgctgc gtgctgctgc tgtgtggcgc cgtgtttgtg  60
agcaatagca tgggcgccgc cgccagcatc cagaccaccg ttaataccct gagcgagaga 120
atctccagca agctggagca ggaggccaat gccagcgccc agaccaagtg tgatatcgag 180
atcggcaact tctacatcag gcagaaccac ggctgtaata tcaccgtgaa gaacatgtgt 240
tccgccgacg ccgacgccca gctggacgct gttctgagcg ccgccaccga gacctactcc 300
ggcctgacac ccgagcagaa ggcctacgtg cccgccatgt tcaccgccgc cctgaacatc 360
cagacaagcg tgaacacagt ggtgagagat ttcgagaatt acgtgaagca gacatgcaac 420
tcctccgccg tggtggataa caagctgaag atccagaatg tgatcatcga tgagtgctac 480
ggcgcccctg gctcccccac aaacctggag tttatcaata ccggctcctc aaggggcaat 540
tgcgccatca aggccctgat gcagctgacc acaaaggcca ccaccacaaa tctgtgcccc 600
ttccacgagg tgttcaacgc caccacattc gcctccgtgt acgcctggaa taggaagaga 660
atctccaact gcgtggccga ttacagcgtg atctacaatt tcgcccccct ttttgccttt 720
aagtgctacg gcgtgagccc caccaagctg aatgacctgt gctttaccaa tgtgtacgcc 780
gatagctttg tgatcagggg caatgaggtg agccagatcg cccctggcca gaccggcaat 840
atcgccgatt acaactacaa gctgcccgac gatttcacag gctgtgtgat cgcctggaat 900
agcaataagc tggattccaa ggtgggcggc aactacaatt acctgtacag gctgttcaga 960
aagtccaagc tgaagccctt cgagagagac atcagcaccg agatctacca ggccggcaac 1020
agaccttgca atggcgtgga gggcttcaac tgctacagcc ctctgcagag ctacggcttc 1080
aggcccaccc acggcgtggg ccaccagcca tacggggtgg tggtgctgtc cttcgagctg 1140
ctgcacgccc ctgccacagt gtgcggccct aagaagtcca ccaacctggt gaagaataag 1200
tgcgtgaatt ttagagtgca gcctaccgag agcatcgtga ggtttccaa catcacaaat 1260
ctgtgtccct tccacgaagt gtttaatgcc accacatttg cctccgtgta tgcctggaac 1320
agaaagagaa tcagcaactg tgtggccgac tacagcgtga tctataactt tgcccccttc 1380
ttcgccttta aatgttacgg cgtgtcccct accaagctga acgatctgtg ttttaccaat 1440
gtctacgccg attccttcgt gatcagaggc aacgaggtgt cccagatcgc cccaggccag 1500
acaggcaata tcgctgacta caactacaaa ctgcccgatg atttaccgg ctgtgtgatt 1560
gcctggaata gtaacaagct ggacagcaag ccctccggca actacaacta cctgtaccgg 1620
ctgctgagaa agtccaaact gaagcccttt gagagagaca tttccacaga gatctaccaa 1680
gccggcaaca agccctgtaa gggcgtggcc ggcctaatt gctactcccc tctgcagtcc 1740
tacggcttta gacccacata cggcgtggga caccagcct acagggtggt cgtgctgtcc 1800
tttgagctgc tgcatgcccc cgccacagtg tgtggcaagg agagctgcaa cggcctgtac 1860
taccagggca gctgttacat cctgcacagc gactacaagt ccttcgagga cgccaaggcc 1920
aattgcgccg ccgagagctc cacactgcct aacaagtccg acgtgctgac aacatggctg 1980
atcgattacg tggaggatac ctgggctcc gatggcaatc ctatcaccaa gacaacatcc 2040
gactaccagg attccgatgt gtcccaggag gtgagaaagt acttctgcac c          2091

SEQ ID NO: 4           moltype = AA   length = 697
FEATURE                Location/Qualifiers
source                 1..697
                       mol_type = protein
                       organism = unidentified
SEQUENCE: 4
MDAMKRGLCC VLLLCGAVFV SNSMGAAASI QTTVNTLSER ISSKLEQEAN ASAQTKCDIE  60
IGNFYIRQNH GCNITVKNMC SADADAQLDA VLSAATETYS GLTPEQKAYV PAMFTAALNI 120
QTSVNTVVRD FENYVKQTCN SSAVVDNKLK IQNVIIDECY GAPGSPTNLE FINTGSSKGN 180
CAIKALMQLT TKATTTNLCP FHEVFNATTF ASVYAWNRKR ISNCVADYSV IYNFAPFFAF 240
KCYGVSPTKL NDLCFTNVYA DSFVIRGNEV SQIAPGQTGN IADYNYKLPD DFTGCVIAWN 300
SNKLDSKVGG NYNYLYRLFR KSKLKPFERD ISTEIYQAGN RPCNGVEGFN CYSPLQSYGF 360
RPTYGVGHQP YRVVVLSFEL LHAPATVCGP KKSTNLVKNK CVNFRVQPTE SIVRFPNITN 420
LCPFHEVFNA TTFASVYAWN RKRISNCVAD YSVIYNFAPF FAFKCYGVSP TKLNDLCFTN 480
VYADSFVIRG NEVSQIAPGQ TGNIADYNYK LPDDFTGCVI AWNSNKLDSK PSGNYNYLYR 540
LLRKSKLKPF ERDISTEIYQ AGNKPCKGVA GPNCYSPLQS YGRPTYGVG HQPYRVVVLS 600
FELLHAPATV CGKESCNGLY YQGSCYILHS DYKSFEDAKA NCAAESSTLP NKSDVLTTWL 660
IDYVEDTWGS DGNPITKTTS DYQDSDVSQE VRKYFCT                          697
```

| SEQ ID NO: 5 | moltype = DNA length = 19 | |
|---|---|---|
| FEATURE | Location/Qualifiers | |
| source | 1..19 | |
| | mol_type = other DNA | |
| | organism = unidentified | |
| SEQUENCE: 5 | | |
| taatacgact cactatagg | | 19 |

| SEQ ID NO: 6 | moltype = DNA length = 41 | |
|---|---|---|
| FEATURE | Location/Qualifiers | |
| source | 1..41 | |
| | mol_type = other DNA | |
| | organism = unidentified | |
| SEQUENCE: 6 | | |
| gggactcttc tggtccccac agactcagag agaacgccac c | | 41 |

| SEQ ID NO: 7 | moltype = DNA length = 110 | |
|---|---|---|
| FEATURE | Location/Qualifiers | |
| source | 1..110 | |
| | mol_type = other DNA | |
| | organism = unidentified | |
| SEQUENCE: 7 | | |
| gctggagcct cggtggccta gcttcttgcc ccttgggcct ccccccagcc cctcctcccc | | 60 |
| ttcctgcacc cgtaccccg tggtctttga ataaagtctg agtgggcggc | | 110 |

SEQ ID NO: 8    moltype = DNA   length = 585
FEATURE         Location/Qualifiers
source          1..585
                mol_type = other DNA
                organism = unidentified
SEQUENCE: 8
atggacgcca tgaagagagg cctgtgctgt gtgctgctgc tgtgtggcgc cgtgttcgtg   60
tccaactcca tgggcgccgc cgccagcatc cagacaaccg tgaacaccct gtccgagaga   120
atcagcagca agctggagca ggaggccaat gcctccgccc agacaaagtg cgacatcgag   180
atcggcaact tttacatcag gcagaaccac ggctgcaaca tcaccgtgaa gaatatgtgc   240
agcgccgatg ccgatgccca gctggatgcc gtgctgagcg ccgctaccga gacctactcc   300
ggcctgaccc ctgagcagaa ggcctacgtg cccgccatgt tcaccgccgc cctgaacatc   360
cagaccagcg tgaacaccgt ggtgagagat tttgagaact acgtgaagca gacatgcaac   420
tccagcgccg tggtggacaa taagctgaag atccgaacga tgatcatcga tgagtgctac   480
ggcgcccctg gctcccctac aaaacctgga g tttatcaaca ccggctccag caagggcaac   540
tgtgccatca aggccctgat gcagctgacc accaaggcca ccaca               585

SEQ ID NO: 9    moltype = DNA   length = 696
FEATURE         Location/Qualifiers
source          1..696
                mol_type = other DNA
                organism = unidentified
SEQUENCE: 9
atggacgcca tgaagagggg cctgtgctgt gtgctgctgc tgtgcggcgc cgtgttcgtg   60
agcaattcca caaacctgtg tccttttcac gaggtgttca acgccacaac cttcgccagc  120
gtgtgcgcct ggaacaggaa gagaatcagc aattgtgtgc ccgactacag cgtgatcgac  180
aacttcgccc cttctcttgc ctttaagtgc tacggcgtga gccctacaaa gctgaacgac  240
ctgtgcttta caaatgtgta cgccgatagc ttcgtgatca gaggcaacga ggtgagccag  300
atcgccctg ccagaccgg caacatcgcc gattacaatt acaagctgcc cgacgatttt  360
accggctgtg tgatcgcctg gaacagcaac aagctggact ccaaggtggg cggcaattac  420
aattacctgt acaggctgtt taggaagtcc aagctgaagc cttttgagag ggatatctcc  480
accgagatct accaggccgg caacaggccc tgtaacggcg tggagggctt caattgctac  540
agccctctgc agtcctacgg cttcagacct acctacggcg tgggccacca gccttacagg  600
gtggtggtgc tgagcttcga gctgctgcac gccccgcca cagtgtgcgg acctaagaag  660
tccacaaatc tggtgaagaa taagtgtgtg aacttc                       696

SEQ ID NO: 10   moltype = DNA   length = 324
FEATURE         Location/Qualifiers
source          1..324
                mol_type = other DNA
                organism = unidentified
SEQUENCE: 10
atggacgcca tgaagagggg cctgtgttgt gtgctgctgc tgtgcggcgc cgtgttcgtg   60
tccaacagca aggagagctg taatggcctg tactaccagg gcagcggtta catcctgcac   120
agcgactaca gtccttcga ggacgccaag gccaattgtg ccgccgagag cagcacactg   180
cctaataaga gcgacgtgct gacaacctgg ctgatcgatt acgtgaagga tacctgggc   240
agcgacggca tcctatcac aaagacaacc tccgactacc aggattccga tgtgtcccag   300
gaggtgagga agtacttttg caca                                       324

SEQ ID NO: 11   moltype = RNA   length = 855
FEATURE         Location/Qualifiers
source          1..855
                mol_type = mRNA
                organism = unidentified -continued

```
SEQUENCE: 11
gggactcttc tggtcccac  agactcagag agaacgccac catggacgcc atgaagagag   60
gcctgtgctg tgtgctgctg ctgtgtggcg ccgtgttcgt gtccaactcc atgggcgccg  120
ccgccagcat ccagacaacc gtgaacaccc tgtccgagag aatcagcagc aagctggagc  180
aggaggccaa tgcctccgcc cagacaaagt gcgacatcga gatcggctac ttttacatca  240
ggcagaacca cggctgcaac atcaccgtga agaatatgtg cagcgccgat gccgatgccc  300
agctggatgc cgtgctgagc gccgctaccg agacctactc cggcctgacc cctgagcaga  360
aggcctacgt gcccgccatg ttcaccgccg ccctgaacat ccagaccagc gtgaacaccg  420
tggtgagaga ttttgagaac tacgtgaagc agacatgcaa ctccagcgcc gtggtggaca  480
ataagctgaa gatccagaac gtgatcatcg atgagtgcta cggcgccccct ggctcccta   540
caaacctgga gtttatcaac accggctcca gcaagggcaa ctgtgccatc aaggccctga  600
tgcagctgac caccaaggcc accacatgat aataggctgg agcctcggtg cctagcttc   660
ttgcccttg gcctccccc cagccctcc tccccttcct gcaccgtac ccccgtggtc  720
tttgaataaa gtctgagtgg gcggcaaaaa aaaaaaaaaa aaaaaaaaaa aaaaaaaaaa  780
aaaaaaaaaa aaaaaaaaaa aaaaaaaaaa aaaaaaaaaa aaaaaaaaaa aaaaaaaaaa  840
aaaaaaaaaa aaaaa                                                   855

SEQ ID NO: 12        moltype = RNA   length = 966
FEATURE              Location/Qualifiers
source               1..966
                     mol_type = mRNA
                     organism = unidentified
SEQUENCE: 12
gggactcttc tggtcccac  agactcagag agaacgccac catggacgcc atgaagaggg   60
gcctgtgctg tgtgctgctg ctgtgcggcg ccgtgttcgt gagcaattcc acaaacctgt  120
gtccttttca cgaggtgttc aacgccacaa ccttcgcca cgtgtacgac tggaacagga  180
agagaatcag caattgtgtg gccgactaca gcgtgatcta caacttcgcc ccttttcttg  240
cctttaagtg ctacgcgtg agccctacaa agctgaacga cctgtgcttt acaaatgtgt  300
acgccgatag cttcgtgatc agaggcaacg aggtgagcca gatcgccct ggccagaccg  360
gcaacatcgc cgattacaat tacaagctgc ccgacgattt cacgctgt gtgatcgcct  420
ggaacagcaa caagctggac tccaaggtgg gcggcaatta caattacctg tacaggctgt  480
ttaggaagtc caagctgaag ccttttgaga gggatatctc caccgagatc taccaggccg  540
gcaacaggc ctgtaacggc gtggagggct tcaattgcta cagccctctg cagtcctacg  600
gcttcagacc taccttacggc gtgggccacc agccttacg ggtggtggtg ctgagcttcg  660
agctgctgca cgccccccgcc acagtgtgcg gacctaagga gtccacaaat ctggtgaaga  720
ataagtgtgt gaacttctga taataggctg gagcctcggt ggcctagctt cttgcccctt  780
gggcctcccc ccagccccctc ctcccctttcc tgcaccgta  ccccgtggt ctttgaataa   840
agtctgagtg ggcggcaaaa aaaaaaaaaa aaaaaaaaaa aaaaaaaaaa aaaaaaaaaa  900
aaaaaaaaaa aaaaaaaaaa aaaaaaaaaa aaaaaaaaaa aaaaaaaaaa aaaaaaaaaa  960
aaaaaa                                                              966

SEQ ID NO: 13        moltype = RNA   length = 594
FEATURE              Location/Qualifiers
source               1..594
                     mol_type = mRNA
                     organism = unidentified
SEQUENCE: 13
gggactcttc tggtcccac  agactcagag agaacgccac catggacgcc atgaagaggg   60
gcctgtgttg tgtgctgctg ctgtgcggcg ccgtgttcgt gtccaacagc aaggagagct  120
gtaatggcct gtactaccag ggcagctgtt acatcctgca cagcgactac aagtccttcg  180
aggacgccaa ggccaattgt gccgccgaga gcagcacact gcctaataag agcgacgtgc  240
tgacaacctg gctgatcgat tacgtggagg atacctgggg cagcgacggc aatcctatca  300
caaagacaac ctccgactac caggattccg atgtgtccca ggaggtgagg aagtactttt  360
gcacatgata ataggctgga gcctcggtgg cctagcttct tgcccttgg gcctcccccc  420
agccccctcc tccccttcctg cacccgtacc cccgtggtct ttgaataaag tctgagtggg  480
cggcaaaaaa aaaaaaaaaa aaaaaaaaaa aaaaaaaaaa aaaaaaaaaa aaaaaaaaaa  540
aaaaaaaaaa aaaaaaaaaa aaaaaaaaaa aaaaaaaaaa aaaaaaaaaa aaaa         594

SEQ ID NO: 14        moltype = RNA   length = 1482
FEATURE              Location/Qualifiers
source               1..1482
                     mol_type = mRNA
                     organism = unidentified
SEQUENCE: 14
gggactcttc tggtcccac  agactcagag agaacgccac catggacgcc atgaagagag   60
gcctgtgctg tgtgctgctg ctgtgcggcg ccgtgttcgt gtccaacagc atgggcgccg  120
ccgccagcat ccagaccaca gtgaataccc tgagcgagag gatcagctcc aagctggagc  180
aggaggccaa tgcagcgcc cagaccaagt gtgatatcga gatcggcaat ttctacatca  240
ggcagaacca cggctgtaac atcacagtga agaatatgtg ctccgccgat gccgatgccc  300
agctggacgc cgtgctgtcc gccgctaccg agacctacag cggcctgaca cctgagcaga  360
aggcctacgt gcctgccatg ttcaccgccg ccctgaacat ccagaccagc gtgaataccg  420
tggtgaggga ttttcgagaat tacgtgaagc agacatgcaa cagcagcgcc gtggtggata  480
acaagctgaa gatccagaat gtgatcatcg acgagtgcta cggcgccccc ggcagcccta  540
caaacctgga gtttatcaac acaggcagca gcaagggcaa ctgtgccatc aaggccctga  600
tgcagctgac aaccaaggcc acaacaacaa acctgtgccc cttcacgag gtgttcaacg   660
ccacaacctt cgcctccgtg tacgctggaa taggaagag gatctccaac tgcgtggccg  720
actactccgt gatctacaac ttcgcccct tttccgcctt taagtgttac ggcgtgagcc  780
ctacaaagct gaatgacctg tgtttcacca atgtgtacgc cgattccttt gtgatcagag  840
gcaacgaggt gtcccagatc gcccccggcc agacaggcaa tatcgccgac tacaactaca  900
```

```
agctgcctga tgacttcacc ggctgtgtga tcgcctggaa tagcaacaag ctggattcca    960
aggtgggcgg caactacaac tacctgtaca ggctgttcag aaagagcaag ctgaagcctt   1020
ttgagagaga catctccacc gagatctacc aggccggcaa cagaccctgt aatggcgtgg   1080
agggcttcaa ttgctactcc cccctgcagt cctacggctt caggcccaca tacggcgtgg   1140
gccaccagcc ctacagagtg gtggtgctga gctttgagct gctgcacgcc cctgccaccg   1200
tgtgcggacc aaagaagtcc acaaatctgg tgaagaacaa gtgcgtgaac tttttgataat   1260
aggctggagc ctcggtggcc tagcttcttg cccctttgggc ctcccccccag ccctcctcc   1320
ccttcctgca cccgtacccc cgtggtcttt gaataaagtc tgagtgggcg gcaaaaaaaa   1380
aaaaaaaaaa aaaaaaaaaa aaaaaaaaaa aaaaaaaaaa aaaaaaaaaa aaaaaaaaaa   1440
aaaaaaaaaa aaaaaaaaaa aaaaaaaaaa aaaaaaaaaa aa                      1482

SEQ ID NO: 15           moltype = RNA   length = 2361
FEATURE                 Location/Qualifiers
source                  1..2361
                        mol_type = mRNA
                        organism = unidentified
SEQUENCE: 15
gggactcttc tggtccccac agactcagag agaacgccac catggatgcc atgaagagag     60
gcctgtgctg cgtgctgctg ctgtgtggcg ccgtgtttgt gagcaatagc atgggcgccg    120
ccgccagcat ccagaccacc gttaataccc tgagcgagag aatctccagc aagctggagc    180
aggaggccaa tgccagcgcc cagaccaagt gtgatatcga gatcggcaac ttctacatca    240
ggcagaacca cggctgtaat atcaccgtga agaacatgtg ttccgccgac gccgacgccc    300
agctggacgc tgttctgagc gccgccaccg agacctactc cggcctgaca cccgagcaga    360
aggcctacgt gcccgccatg ttcacagccg ccctgaacat ccagacaagc gtgaacacag    420
tggtgagaga tttcgagaat tacgtgaagc agacatgcaa ctcctccgcc gtggtggata    480
acaagctgaa gatccagaat gtgatcatcg atgagtgcta cggcgcccct ggctccccca    540
caaacctgga gtttatcaat accggctcct ccaagggcaa ttgcgccatc aaggcctga     600
tgcagctgac cacaaaggcc accaccacaa atctgtgccc cttccacgag gtgttcaacg    660
ccaccacatt cgcctccgtg tacgcctgga ataggaagag aatctccaac tgcgtggccg    720
attacagcgt gatctacaat ttcgcccct tttcgccctt taagtgctac ggcgtgagcc    780
ccaccaagct gaatgacctg tgctttacca atgtgtacgc cgatagcttt gtgatcaggg    840
gcaatgaggt gagccagatc gcccctggcc agaccggcaa tatcgccgat tacaactaca    900
agctgcccga cgatttcaca ggctgtgtga tcgcctggaa tagcaataag ctggattcca    960
aggtgggcgg caactacaat tacctgtaca ggctgttcag aaagtccaag ctgaagccct   1020
tcgagagaga catcagcacc gagatctacc aggccggcaa cagaccttgc aatggcgtgg   1080
agggcttcaa ctgctacagc cctctgcaga gctacggctt caggcccacc tacggcgtgg   1140
gccaccagcc atacagggtg gtggtgctgt ccttcgagct gctgcacgcc cctgccacag   1200
tgtgcggcc taagaagtcc accaacctgg tgaagaataa gtgcgtgaat tttagagtgc   1260
agcctaccga gagcatcgtg aggtttccca acatcacaaa tctgtgtccc ttccacgaag   1320
tgtttaatgc caccacattt gcctccgtgt atgcctggaa cagaaagaga atcagcaact   1380
gtgtggccga ctacacgtg atctataact ttgcccctt cttcgccttt aaatgttacg   1440
gcgtgtcccc taccaagctg aacgatctgt gttttaccaa tgtctacgcc gattccttcg   1500
tgatcagagg caacgaggtg tcccagatcg ccccaggcca gaccggcaat atcgctgact   1560
acaactacaa actgcccgat gattttaccg gctgtgtgat tgcctggaat agtaacaagc   1620
tggacagcaa gccctccggc aactacaact acctgtaccg gctgctgaga aagtccaaac   1680
tgaagcctt tgagagagac atttccacag agatctacca agccggcaac aagccctgta   1740
agggcgtggc cggcctaat tgctactccc ctctgcagtc ctacggcttt agacccacat   1800
acggcgtggg acaccagccc tacagggtgg tcgtgctgtc ctttgagctg ctgcatgccc   1860
ccgccacagt gtgtggcaag gagagctgca acggcctgta ctaccagggc agctgttaca   1920
tcctgcacag cgactacaag tccttcgagg acgccaaggc caattgcgcc gccgagagct   1980
ccacactgcc taacaagtcc gacgtgctga caacatggct gatcgattac gtggaggata   2040
cctgggctc cgatgcaat cctatcacca agacaacatc cgactaccag gattccgatg   2100
tgcccagga ggtgagaaag tacttctgca cctgataata ggctggagcc tcggtggcct   2160
agcttcttgc cccttgggcc tccccccagc ccctcctccc cttcctgcac ccgtaccccc   2220
gtggtctttg aataaagtct gagtgggcgg caaaaaaaaa aaaaaaaaaa aaaaaaaaaa   2280
aaaaaaaaaa aaaaaaaaaa aaaaaaaaaa aaaaaaaaaa aaaaaaaaaa aaaaaaaaaa   2340
aaaaaaaaaa aaaaaaaaaa a                                             2361
```